US012588805B2

(12) United States Patent
    Carruthers et al.

(10) Patent No.: US 12,588,805 B2
(45) Date of Patent: Mar. 31, 2026

(54) SYSTEM FOR TELESCOPING MEMBERS THROUGH AN ELONGATE TUBE

(71) Applicant: Cook Medical Technologies LLC, Bloomington, IN (US)

(72) Inventors: Christopher A. Carruthers, Winston-Salem, NC (US); Liam Breen, Ballina (IE); John Crowder Sigmon, Jr., Winston-Salem, NC (US); Shaun D. Gittard, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 412 days.

(21) Appl. No.: 18/310,878

(22) Filed: May 2, 2023

(65) Prior Publication Data

US 2023/0355082 A1    Nov. 9, 2023

Related U.S. Application Data

(60) Provisional application No. 63/337,886, filed on May 3, 2022.

(51) Int. Cl.
    A61B 1/00        (2006.01)
    A61B 1/018       (2006.01)
(52) U.S. Cl.
    CPC .......... A61B 1/018 (2013.01); A61B 1/00042 (2022.02); A61B 1/00119 (2013.01); A61B 1/00137 (2013.01)
(58) Field of Classification Search
    CPC . A61B 1/018; A61B 1/00042; A61B 1/00119; A61B 1/00137; A61B 1/0014; A61B 1/00066; A61B 1/00174
    See application file for complete search history.

(56) References Cited

U.S. PATENT DOCUMENTS 4,791,912 A  *  12/1988  Tashiro .............. A61B 1/00137
                                                    600/153
5,910,105 A      6/1999  Swain et al.
                (Continued)

FOREIGN PATENT DOCUMENTS

WO      WO 1998/046143 A1    10/1998
WO      WO 2006/033671 A2     3/2006
                (Continued)

OTHER PUBLICATIONS

International Search Report and Written Opinion for PCT Application No. PCT/US2023/066376, dated Oct. 2, 2023, 14 pages.

*Primary Examiner* — Timothy J Neal
(74) *Attorney, Agent, or Firm* — Vivacqua Crane, PLLC

(57) ABSTRACT

An endoscopic device is provided. The endoscopic device may comprise a distal end and a proximal end. The proximal end may be opposite the distal end. The endoscopic device may further comprise a handle at the proximal end and a tube extending from the handle towards the distal end of the endoscopic device. The endoscopic device may further comprise an accessory channel. The accessory channel may extend through the tube. The endoscopic device may further comprise a slide, the accessory channel extending through the slide, and a curved track disposed adjacent to the proximal end of the endoscopic device. The slide is movable within the curved track to cause movement of the accessory channel within the tube.

20 Claims, 8 Drawing Sheets

(56)        References Cited

U.S. PATENT DOCUMENTS

| | | | |
|---|---|---|---|
| 7,566,300 | B2 | 7/2009 | Devierre et al. |
| 8,771,171 | B2 | 7/2014 | Onuki et al. |
| 9,144,396 | B2 | 9/2015 | Choe et al. |
| 9,668,641 | B2 | 6/2017 | Ostrovsky et al. |
| 9,986,996 | B2 | 6/2018 | Hiernaux et al. |
| 10,624,617 | B2 | 4/2020 | Matthison-Hansen et al. |
| 10,835,341 | B2 | 11/2020 | Baril et al. |
| 2010/0256446 | A1* | 10/2010 | Raju ................. A61B 1/00091 |
| | | | 600/114 |
| 2017/0135562 | A1* | 5/2017 | Surti ..................... A61B 1/008 |
| 2017/0251910 | A1* | 9/2017 | Surti ................. A61B 1/00128 |
| 2019/0208990 | A1 | 7/2019 | Chelala et al. |
| 2019/0380562 | A1 | 12/2019 | Deuel et al. |
| 2020/0229680 | A1 | 7/2020 | Matthison-Hansen et al. |
| 2022/0071482 | A1 | 3/2022 | Yee et al. |

FOREIGN PATENT DOCUMENTS

| | | |
|---|---|---|
| WO | WO 2012/111761 A1 | 8/2012 |
| WO | WO 2015/052320 A1 | 4/2015 |
| WO | WO 2016/188540 A1 | 12/2016 |
| WO | WO 2019/055359 A1 | 3/2019 |
| WO | WO 2019/246266 A1 | 12/2019 |
| WO | WO 2019/246275 A1 | 12/2019 |
| WO | WO 2019/246277 A1 | 12/2019 |

* cited by examiner

SYSTEM FOR TELESCOPING MEMBERS THROUGH AN ELONGATE TUBE

CROSS-REFERENCE TO RELATED APPLICATIONS

The present application claims the benefit of U.S. Provisional Application No. 63/337,886, filed May 3, 2022, which is incorporated by reference herein in its entirety for all purposes.

FIELD

The present disclosure relates to medical devices and more specifically to endoscope systems.

BACKGROUND

The statements in this section merely provide background information related to the present disclosure and may not constitute prior art.

The traditional endoscope is a medical device used in a variety of procedures. A physician may insert the endoscope, for example, into a patient's mouth and through the patient's gastrointestinal (GI) tract. The physician may then use a variety of instruments during the procedure that are passed through an accessory channel that is located within the outer shaft of the endoscope. As the endoscopy field advances, new endoscopes are being created for specific procedures that change how the physician holds and operates the endoscope.

Traditional endoscopes have one or more accessory channels that are of fixed length, and are fixed at the proximal and distal end of the endoscope. In this case, the physician only needs to advance or retract the accessory relative to the accessory channel while the accessory channel remains stationary.

One example of a novel endoscope is one that allows the physician to advance or retract the accessory channels relative to the outer shaft, and independently advance or retract the accessories relative to the accessory channels. The movement of the accessories and accessory channels is performed at the handle of the endoscope. This endoscope is described in U.S.20210369090A1.

As the physician holds this novel endoscope, the physician only has one available hand to control the extension of the accessory channel and/or instruments that pass through the accessory channel. This is because the physician's other hand is usually occupied with controlling the steering of the endoscope and various control buttons of the endoscope that control lens washing, insufflation, suction, and camera functions. The physician may have a nurse assistant who typically controls the devices that are passed through the accessory channel. However, physicians prefer to have control over the extension and retraction of the accessory channels themselves if possible, and extension and retraction of the accessories relative to the accessory channel. During the procedure, the physician requires the accessory channels to remain stationary at their relative position while they advance the accessories through them. In some scenarios, the physician requires the accessory channels and the accessories to move simultaneously. Thus, it is desirable to provide a function to the described novel endoscope system that is capable of stabilizing and supporting the accessory channel so they can use their hand to manipulate the accessory and do not have to constantly hold the accessory channel.

In addition to the challenge of accessory channel and accessory management, the physician also has a need for coarse, or relatively larger movement of the accessory channel as well as fine, or relatively smaller, more precise movement of tubing. For example, during cannulation of a bile duct, the physician needs fine adjustment capability. On the other hand, when a quick movement of tubing is needed, the physician may want a coarse movement in order to not delay the procedure, especially if they have to repeatedly make that movement.

In summary, in the case of the described novel endoscope, the physician requires the ability to independently control the accessory channels and the accessories that pass through them using only one hand. Is it desirable to be able to move the accessory channels and accessories independtly or simultaneously, depending on the clinical scenario, and in varying degrees of coarse or fine movement. Due to the fact the physician only has one available hand to execute these actions, the novel endoscope described requires features that make these movements possible in a controlled fashion.

SUMMARY

In one form of the present disclosure, an endoscopic device is provided. The endoscopic device may comprise a distal end and a proximal end. The proximal end may be opposite the distal end. The endoscopic device may further comprise a handle at the proximal end and a tube extending from the handle towards the distal end of the endoscopic device. The endoscopic device may further comprise an accessory channel. The accessory channel may extend through the tube. The endoscopic device may further comprise a sliding guide, the accessory channel extending through the sliding guide, and a track disposed adjacent to the proximal end of the endoscopic device. The track may, for example, be curved, straight, or any other suitable shape and/or profile. The sliding guide is movable within the track to cause movement of the accessory channel within the tube. The endoscopic device may further include an access port integrated with the sliding guide, such that the access port moves when the sliding guide moves within track. The endoscopic device may further comprise a roller assembly disposed in the distal end of the handle.

Further areas of applicability will become apparent from the description provided herein. It should be understood that the description and specific examples are intended for purposes of illustration only and are not intended to limit the scope of the present disclosure.

BRIEF DESCRIPTION OF DRAWINGS

The drawings described herein are for illustration purposes only and are not intended to limit the scope of the present disclosure in any way.

DETAILED DESCRIPTION

Figure 1A:
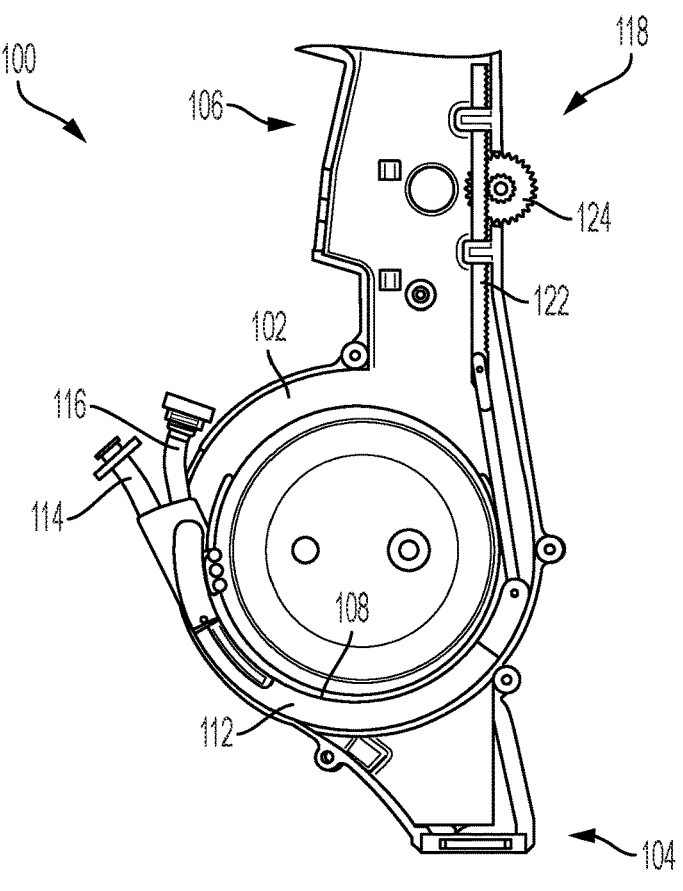
FIGS. 1A and 1B illustrate an example of an endoscope system.

The following description is merely exemplary in nature and is not intended to limit the present disclosure, application, or uses. It should be understood that throughout the drawings, corresponding reference numerals indicate like or corresponding parts and features.

Figure 1B:
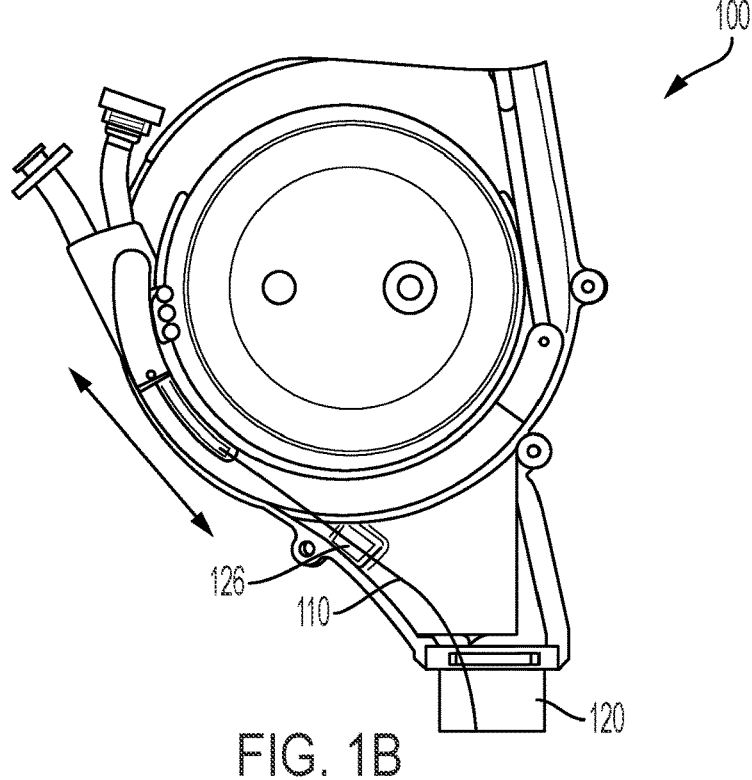

Referring to FIGS. 1A-B, an endoscope system 100 is provided. The endoscope system 100 may be generally shaped as an elongate tube including a distal portion (shown in FIGS. 8A-D), a proximal portion or handle 102, and a central portion including the tube 120 that extends between the handle 102 and the distal portion. As shown (and without limitation), the endoscope system 100 may comprise the handle 102 with a distal end 104 and a proximal end 106, a track 108, an accessory channel 110, a sliding member 112, one or more access ports 114, 116, a fine adjustment system or actuator 118, and a tube 120.

The track 108 may be disposed inside of the handle 102, and the sliding member 112 may fit along the track 108. In the depicted emboidment, the sliding member 112 may be a slide or other movable piece that has a curved contour matching a curved countour of the track 108, which is discussed in more detail below, but the sliding member 112 may be a slide of any other suitable shape, for example, the sliding member 112 may be straight. The accessory channel 110 may be connected to and extend through the sliding member 112 such that movement of the sliding member 112 advances and retracts the accessory channel 110. The access ports 114, 116 may be connected to the accessory channel 110 and extend through the handle 102 to provide access to the accessory channel 110 from outside of the endoscope system 100. The access ports 114, 116 may also be attached to the sliding member 112. The actuator 118 may include, for example, a rack 122 and pinion 124. The actuator 118 may be connected to the sliding member 112 at the opposite of the sliding member 112 from the access port(s) 114, 116. A tube 120 may be connected to the distal end 104 of the handle 102. The accessory channel 110 may extend from the access ports 114, 116, through a body of the handle 102, and through the tube 120.

The handle 102 may comprise a casing that encases the track 108, the sliding member 112, the actuator 118, a at least part of the accessory channel 110 and the access ports 114, 116. The handle 102 may have a distal end 104 and a proximal end 106, wherein, when being used for a procedure, the distal end 104 refers to the end of the handle 102 disposed closer to a patient's body and the proximal end 106 refers to the end of the handle disposed farther from the patient. The handle 102 may be ergonomically shaped for comfort for the physician as they hold the handle 102 during a procedure. For example, the handle 102 may comprise a grip support. The body or central portion of the handle disposed between the distal end 104 and proximal end 106 may be, for example, curved (e.g., semi-circular) in order to accommodate the track 108 and sliding member 112. The handle 102 may be made of, for example, plastic, for example a molded plastic, or metal, and/or any other suitable material.

The handle 102 is merely one potential embodiment of a handle for the endoxcope system 100, and any other compatible handle design capable of controlling the endoscope system 100 may be used, including variations on the arms or sliding members 112 that control various features of the system 100. The handle 102 and various controls such as the accessory channels 110, access ports 114, 116, actuator 118, and/or sliding member 112 may include locking elements that lock the system in the various configurations. In certain examples, the handle 102 may include frictional locks, where the various bodies, ports, and sliding members may be maintained in their current position with a frictional force. However, an externally-applied force may overcome the frictional force and still move the controls when desired.

The track 108 may be disposed within the handle 102. The track 108, for example, may be integral with the handle 102 such that the handle 102 casing and the track 108 are one integral, continuous piece. Alternatively, the track 108 may be a separate component from the remainder of the handle 102 that is secured to the remainder of the handle 102. The track 108 may comprise the same or different material as the handle 102, for example, a plastic or metal, or any other suitable material. The track or sliding member may be coated with a lubricious substance such as Teflon or silicone grease to miminize friction and resistance to the user to actuate the sliding member. Additionally, resistance features such as bumps may be added to fine tune the resistance so the user doesn't accidentally engage the sliding member when manipulating accessories. These features may also be selectively placed to indicate a specific position to the user via resistance or an audible noise.

The track 108 may be disposed within the body or central portion of the handle 102 between the distal end 104 and the proximate end 106 of the handle. The track 108 may form any shape capable of allowing movement of the sliding member 112 when it is slid along the track 108. For example, the track 108 may be curved. The track 108, for example, may be semi-circular or semi-ovular in shape. The track 108 may be shaped similar to the central portion of the handle 102. For example, the central portion of the handle 102 may be circular in shape, with a radius of an outer perimeter curve of the track 108 being smaller in size than a radius of the handle 102 such that there is a constant gap between the track 108 and the handle 102 around the entire circumference of the track 108. Additionally or alternatively, the track 108 may be at least partially defined by the handle 102, for example, by an inner diameter of a circular portion of the handle 102. For example, the sliding member 112 may contact the inner diameter surface of the handle 102 shell.

The sliding member 112 may be any component able to slide or move along the track 108. For example, the sliding member 112 may comprise a plurality of rollers or bearings. Alternatively or additionally, the track 108 may contain rollers or bearings. Alternatively or additionally, the sliding member may comprise a low-friction contact surface that slides along a radially outer surface of the track 108. Alternatively, the sliding member may comprise multiple telescoping members that fit within each other and extend and collapse in order to advance and retract. The sliding member 112 may be shaped to fit along the track. For example, the track 108 and sliding member 112 may both be curved. For example the track 108 may be semi-circular (i.e., a curving having an approximately constant radius), and the sliding member 112 may be in the shape of an arc having a corresponding radius for fitting with the outer circumference of the track 108. The center of the sliding member 112 may have a radius that is larger than a radius of the track 108 and smaller than a radius of the central portion of the handle 102. The sliding member 112 may be made of an material capable of sliding along the track 108, for example, plastic or metal or any other suitable material. The sliding member 112 may be comprised entirely of the same material. Additionally or alternatively, the sliding member may comprise multiple different materials, for example, the surface of the sliding member 112 that contacts the track 108 may be a different material than the rest of the sliding member 112.

The access ports 114, 116 may be disposed on a side of the handle 102 and extend through the casing of the handle 102 so that a portion of the access ports 114, 116 are external to the handle 102 and another portion of the access ports 114, 116 extend into the inner compartment of the handle 102 where the track 108 and sliding member 112 are disposed. The handle 102 may comprise a single access port or a plurality of access ports 114, 116. The access ports 114, 116 may be, for example, circular in cross section. The access ports 114, 116 may each comprise a seal. The access ports 114, 116 may optionally be formed of plastic, but other materials are also contemplated. The seal itself may be of a flexible polymer such as silicone. The access ports 114, 116 may, for example, be formed of the same material as the sliding member and/or the accessory channel 110. Additionally or alternatively, the access ports 114, 116 may be formed of a different material than the sliding member 112 and/or accessory channel 110. The portion of the access ports 114, 116, disposed inside of the handle 102 may be connected to the sliding member 112 such that movement of the sliding member causes movement of the access ports 114, 116 relative to the handle 102. The access ports 114, 116 may be detachably connected to the sliding member 112 via a mechanism, such as a clutch, for engaging and disengaging with the sliding member 112, such that when the access ports 114, 116 are disengaged from the sliding member, movement of the sliding member 112 does not cause movement of the access ports 114, 116.

The accessory channel 110 may also be referred to as an elongated body or tube, and may be any component or formation extending from the handle to the distal end of the endoscope system 100 and able to move with respect to the tube 120. The endoscopic system 100 may comprise a plurality of accessory channels 110. The accessory channels 110 may vary in size and shape, for example, to accommodate larger or smaller accessories. For example, the accessory channels 110 may range from system to system. Additionally or alternatively, the accessory channels 110 within the same endoscopic system 100 may range in diameter relative to each other. The accessory channels 110 may be any diameter suitable to fit endoscopic accessories and pass the accessories through the accessory channels 110. A single accessory channel 110 may have multiple accessories running through it. The accessory channel 110 may be, for example, a tube, such as a cylindrical tube. Additionally or alternatively, the accessory channel 110 may be a channel or other hollow formation extending from the handle, for example from the sliding member 112 and/or the access ports 114, 116 to the distal end of the endoscopic device 100. The accessory channel 110 may be made of, for example, plastic or a polymer material. The accessory channel 110 may be used to provide access for a variety of medical tools and accessories through the endoscope system 100 and into a patient's body. For example, a camera system may be inserted into one of the The accessory channel 110 while a variety of tools such as forceps, sphincterotomes, wires, dilation balloons, extraction balloons, stents, needle knives, hemostasis clips, and any other catheter based tool may be inserted into a second accessory channel 110. The tools may be advanced past the distal ends of the accessory channels 110 where they may be used to operate on a patient.

The actuator 118 may be any mechanism capable of enabling relatively fine movement of the sliding member 112 as compared to the surgeon directly feeding components through the access ports 114, 116 and/or directly moving the sliding member 112. The actuator 118 may be attached to an end of the sliding member 112 such that movement of the actuator 118 causes movement of the sliding member 112, and therefore, movement of the accessory channel 110. For example, the actuator 118 may enable fine, controlled movements for relatively shorter distances, for example, for short distances not able to be accurately done by manually advancing the accessories through the ports 114, 116. The actuator 118 may comprise, for example, a rack 122 and pinion 124. The rack 122 may be, for example, a linear rack comprising evenly spaced apart teeth. The pinion 124 may be a geared wheel with teeth that mesh with the teeth on the rack 122. Alternatively, the actuator 118 may comprise different mechanisms, as explained below. The actuator 118 may be made of, for example, plastic or metal (or any other suitable material). The actuator 118 may be made of the same of different material as the sliding member 112.

The tube 120 may be any hollow tube, for example, a circular tube, able to have components extended through it. The tube 120 may be made of a polymer extrusion such as pebax with a polytetrafluoroethylene liner, and may be reinforced with a coil and/or braid construction to provide sufficient torqueability, pushability, and kink resistance. Other potential materials for the central portion 14 include but are not limited to polyethylene, polypropylene, and nylon. The tube 120 may be attached to the distal end of the handle 102 to create a continuous cavity extending from inside of the handle 102 casing and through an opening of the tube 120. The tube 120 may extend to the distal end of the endoscopic system 100. For example, the tube 120 may connect the handle 102 to a distal end of the endoscopic system 100.

During operation the surgeon may insert a distal end of a component or accessory through an access port 114, 116 and into the accessory channel 110. The surgeon may then directly advance or retract the accessory by pushing or pulling a length of the accessory through the access port 114, 116. Additionally or alternatively, the surgeon may advance or retract the accessory and accessory channel 110 through the tube 120 by moving the access port 114, 116 attached to the sliding member 112. The sliding member 112 may then slide along the track 108 and move the accessory channel 110 with respect to the tube 120. Additionally or alternatively, the surgeon may use the actuator 118, for example, by rotating a pinion 124 of the actuator 118 in order to advance or retract the accessory channel 110 and the accessory. Rotation of the pinion 124 may cause upward or downward movement of a rack 122, which in turn moves the sliding member 112 along the track 108. The sliding member 112 may cause movement of the accessory channel 110 and the accessory extending through the accessory channel 110. During operation, the surgeon may advance the accessory channel 110 to and from the distal end of the endoscopic system 100.

Figure 2:
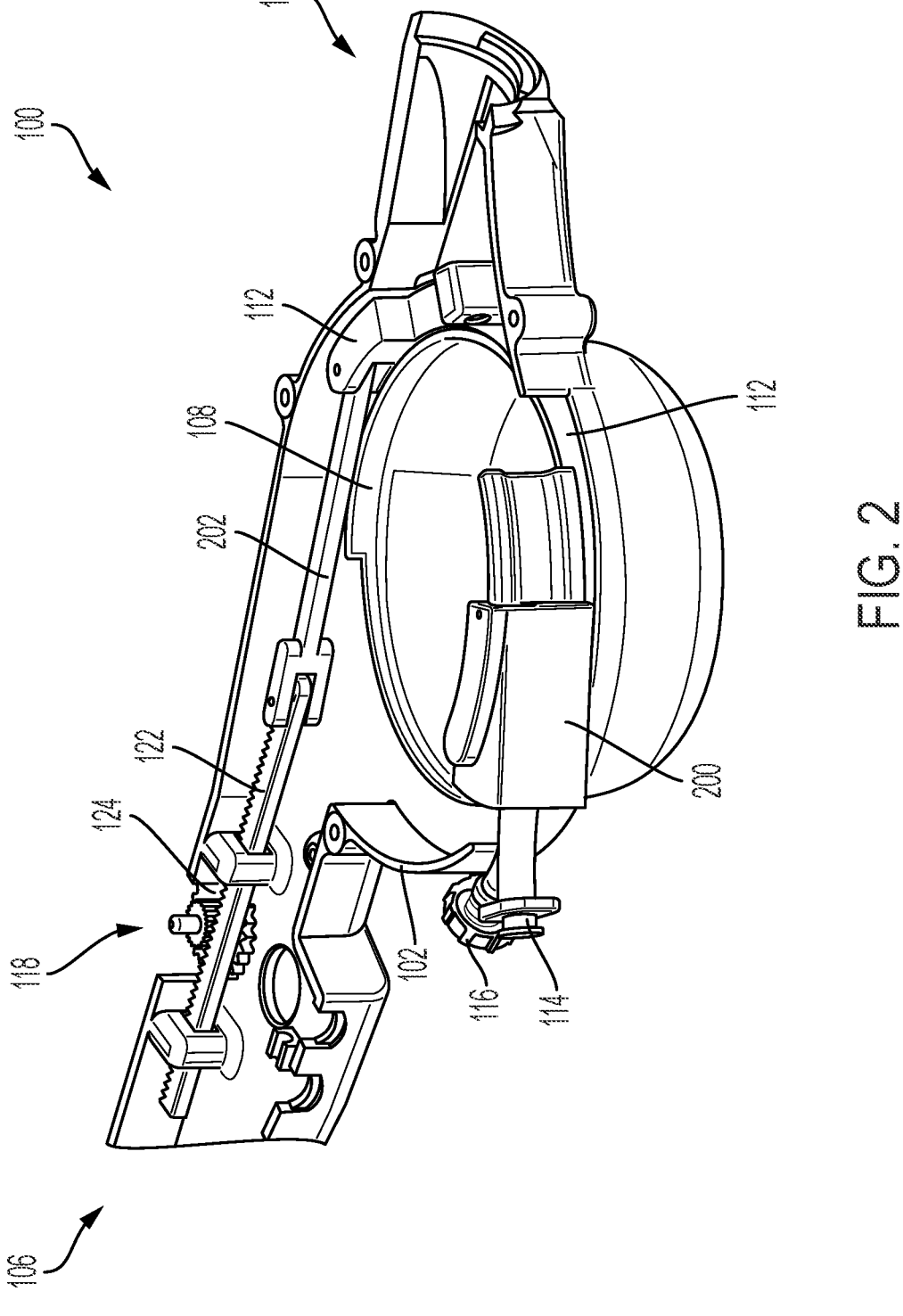
FIG. 2 illustrates another view of the endoscopic system.

FIG. 2 illustrates a another view of the endoscopic system 100 of FIGS. 1A-B with a portion of the handle 102 casing removed. As shown, he endoscopic system 100 may further include a port adapter 200 and a linking arm 202.

The port adapter 200 may connect the access ports 114, 116 to the sliding member 112 and/or the accessory channel 110. The port adapter 200 may be a separate component assembled with the access ports 114, 116 and the sliding member 112, or may be manufactured integrally with the access ports 114, 116 and/or the sliding member 112 such the integral components are all one continuous piece. The port adapter 200 may be made of the same or different material as the access ports 114, 116 and/or sliding member, such as a plastic (or any other suitable material). The port adapter 200 may comprise hollow channels that extend from each of the access ports 114, 116 through the port adapter 200. Accessory channels 110 may fit into the hollow channels of the port adapter 200 so that accessories can be passed through the access ports 114, 116, through the port adapter 200, and into the accessory channel 110. The surgeon may advance the access ports 114, 116 and/or the port adapter in order to achieve relatively coarse or large movements of the accessory channel 110.

The linking arm 202 may removably connect the actuator 118, for example, the rack 122 of the actuator 118, to the sliding member 112. An end of the linking arm 202 may connect to an end of the sliding member 112 opposite from the end connected to the port adapter 200 via a joint, for example, a hinge. An opposite end of the linking arm 202 may connect to an end of the rack 122 via a joint, for example, a hinge. The pivoting action of the joints at the respective ends ofthe linking arm 202 enables the, for example, linear movement of the actuator 118, to cause a curving movement of the sliding member 112. The linking arm 202 may be made of the same or different materials as the rack 122 and/or sliding member 112, for example, a metal of plastic material (or any other suitable material).

Figure 3:
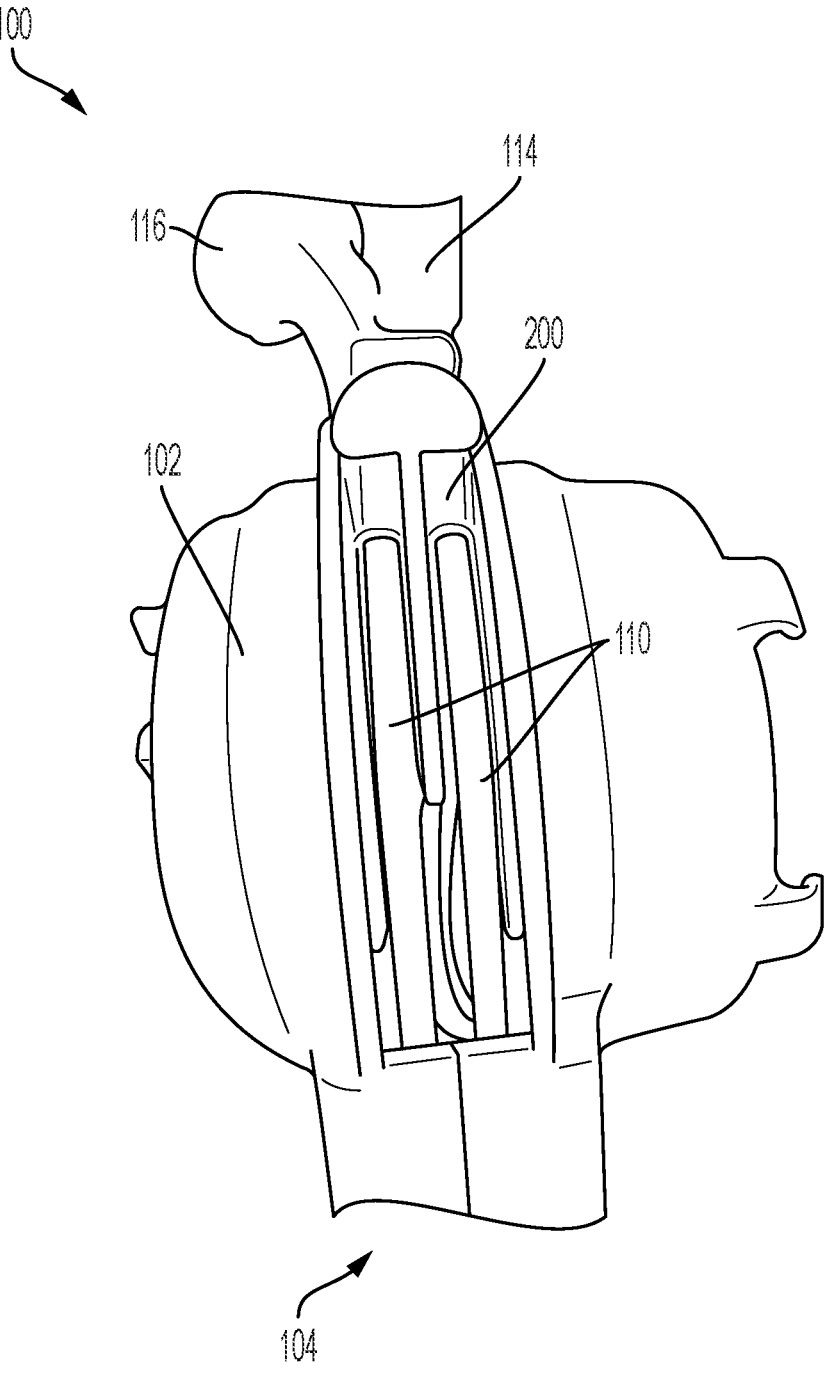
FIG. 3 illustrates another view of the endoscopic system.

FIG. 3 illustrates another view of the endoscopic system 100 of FIGS. 1A-B and FIG. 2 with part of the handle 102 casing removed. FIG. 3 illustrates an example of the endoscopic system 100 including multiple accessory channels 110 and an example of the accessory channels 110 being received by a set of channels of the port adapter 200. These channels may be made not visible to the operator with an accordian structure, or an extension from the handle shell or sliding feature. Such an extension may be rigid, flexible, or a spring mechanism.

Figure 4A:
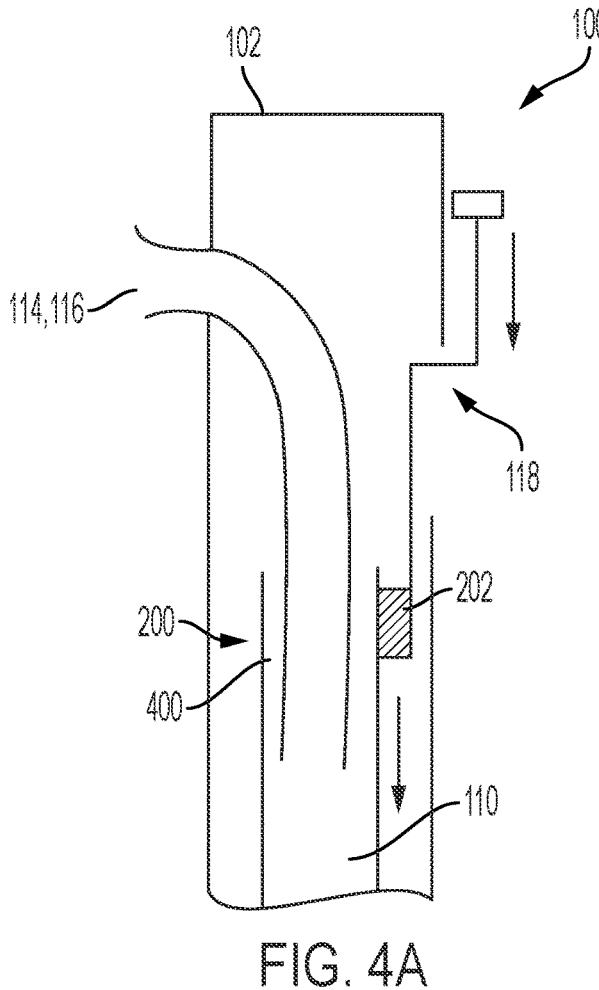
FIGS. 4A and 4B illustrate a schematic view of the endoscopic system.
Figure 4B:
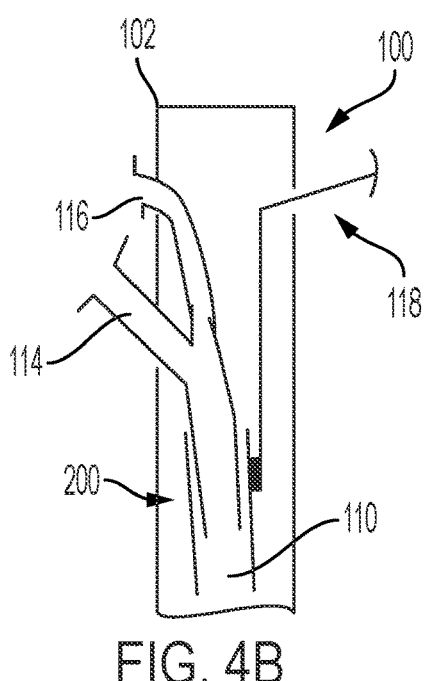

FIGS. 4A and 4B illustrate schematic drawings of the endoscopic system 100 such as those shown in FIGS. 1-3. The linking arm 202, which may also be referred to as a joint, may connect to the sliding member 112 as shown in FIG. 2, or alternatively may connect directly to the accessory channel 110 as shown in FIG. 4A. The port adapter 200 may also include a dynamic seal 400 to create a fluid tight seal between the access ports 114, 116 and the accessory channel 110. The dynamic seal 400 may allow for a fluid tight seal to be maintained between the access ports 114, 116 and the accessory channel 110 as the accessory channel 110 and/or access ports 114, 116 are advanced and retracted with respect to each other and/or with respect to the tube 120. Additionally or alternatively, one of the access ports, for example, access port 116 may be an irrigation port 116 for fluids. The access port 116 may include a seal to create a fluid tight seal between the access port 116 and any accessory or component being advanced or retracted through an external opening of the access port 116 our side of the handle 102 casing.

Figure 5B:
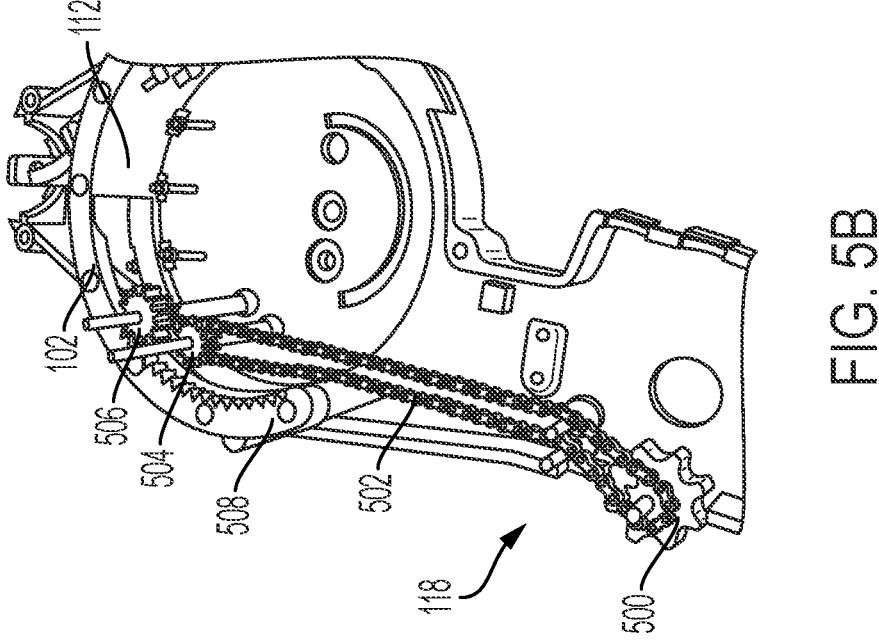
FIGS. 5A and 5B illustrate examples of a fine movement actuator of the endoscopic system.
Figure 5A:
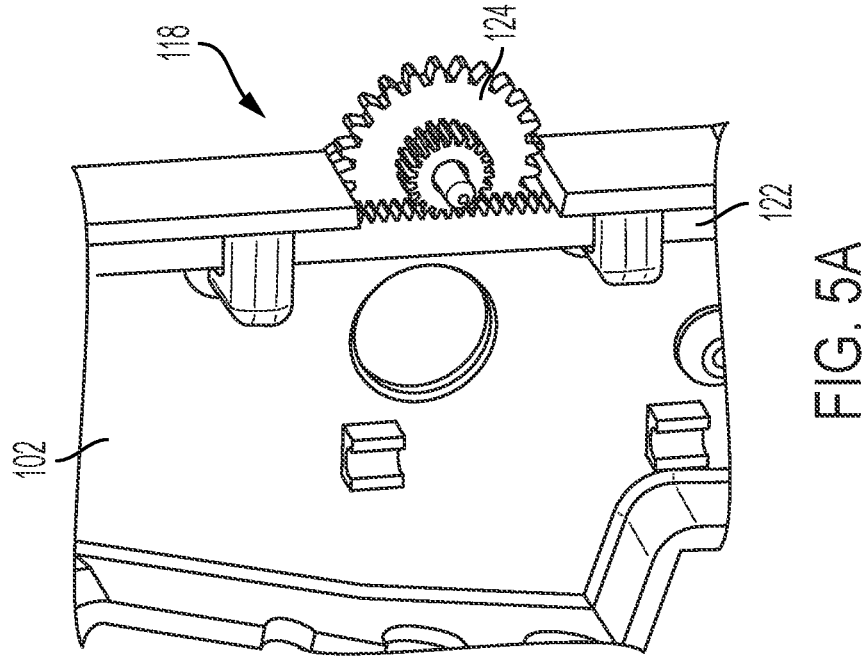

FIGS. 5A-B illustrate example embodiments of the fine movement actuator 118 of the endoscopic system 100 such as the one shown in FIGS. 1-4. FIG. 5A shows the rack 122 and pinion 124 embodiment of the actuator 118 as shown in FIGS. 1-2. FIG. 5B illustrates another embodiment of the actuator 118 comprising a system of a chain 502 and gears 500, 504, 506. The gears 500, 504, 506 may be, for example, spur gears. The chain 502 may be any sort of chain or strap, for example a linked chain, capable of meshing with the teeth of the gears 500, 504. The chain 502 and gears 500, 504, 506 may be made of a metal or plastic materials (or any other suitable material). The chain 502 and gears 500, 504, 506 may all be made of the same material, or may be different materials.

A control gear 500 may be disposed on the side of the handle 102 case, accessible to the surgeon from outside of the handle 102 case. The chain may optionally be formed in a loop, with one end of the chain 502 loop wrapped around the control gear 500, the links of the chain 502 meshed with the teeth of the control gear 500. A secondary gear 504 may be displaced closer to the distal end 104 of the handle 102 than the control gear 500. A second end of the chain 502 loop may be wrapped around the secondary gear 504, the links of the chain 502 meshed with the teeth of the secondary gear 504. A sliding member gear 506 may be disposed adjacent to the secondary gear 504. The teeth of the sliding member gear 506 may be meshed with the teeth of the secondary gear 504. The end of the sliding member 112 closest to the gears 504, 506 may have teeth 508 on, for example, a radially inner surface of the sliding member 112. The teeth of the sliding member gear 506 may fit and mesh with the teeth 508 on the surface of the sliding member 112.

During operation, to cause fine movement, the surgeon may spin or turn the control gear 500. The control gear 500 engages the chain 502 and therefore may cause movement of the chain 502 meshed with the teeth of the control gear 500. The chain 502 further engages the secondary gear 504, and therefore this movement of the chain 502 may cause movement of the secondary gear 504, which in turn may cause the sliding member gear 506 to rotate. This rotation of the sliding member gear 506, which directly engages the sliding member 112, may cause movement of the sliding member 112 along the track 108. In summary, as a result of this mechanical arrangement, the surgeon may directly control movement of the sliding member 112 along the track 108 via manipulation of the control gear 500.

Figure 6A:
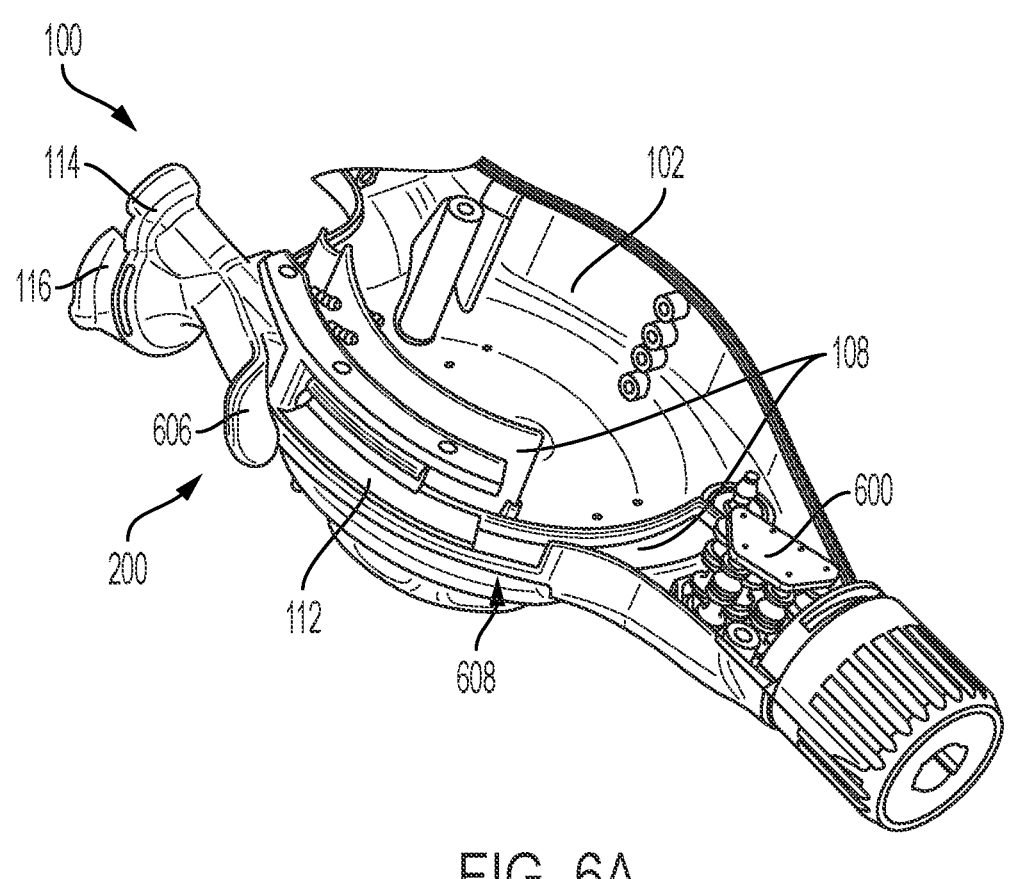
FIGS. 6A and 6B illustrate an example of a roller assembly of the endoscopic system.
Figure 6B:
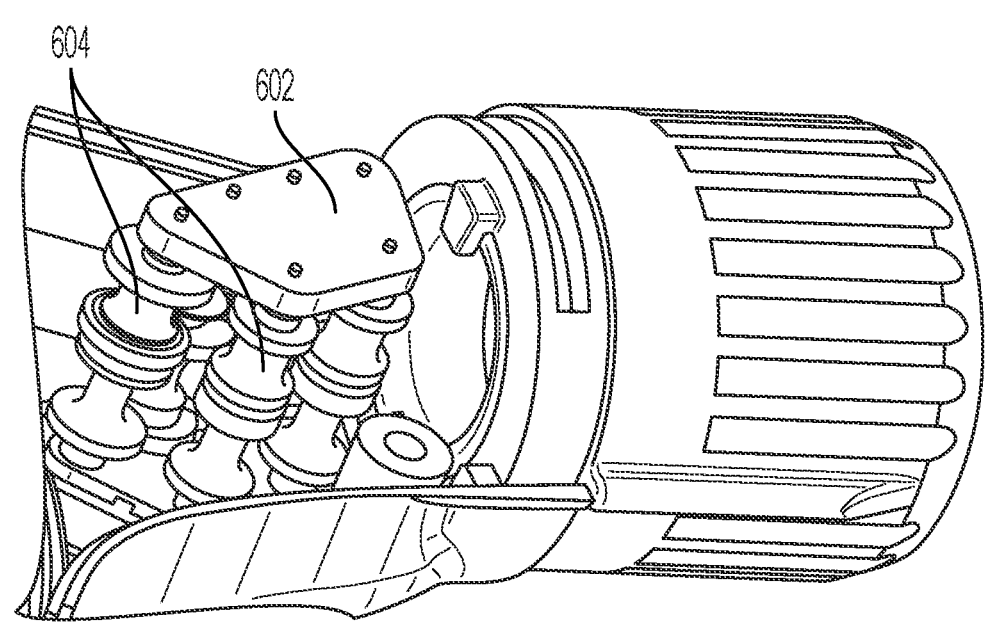

FIGS. 6A-B illustrate another view of the endoscopic system 100, such as the endoscopies system shown in FIGS. 1-5. The endoscopic system 100 may further comprise a roller assembly 600 disposed within the handle 102 casing near the distal end 104 of the handle 102, as shown in FIG. 6A.

FIG. 6A illustrates a more detailed view of the port adapter 200. The ports 114, 116, the port adapter 200, and/or the sliding member 112 may all be a single, unitary component that slides along the track 108. The sliding member 112, port adapter 200, and/or track 108 may be curved. The curve of the sliding member 112, port adapter 200, and/or track 108 may match a curved shape of the handle 102 such that the sliding member 112, port adapter 200, and/or track 108 slide along the curved shape of the handle duing retraction and/or extension of the accessory channel 110.

The track 108 may extend from the port openings 114, 116 to the roller assembly 600 near the distal end of the handle 102, or along any portion therebetween. The curved portion(s) of the port adapter 200 and/or sliding member 112 may be shorter in length than the track 108 and only extend along a portion of the track 108 at a time. The port adapter 200 may include a handle and/or finger rest 606 for the physician to use during operation to advance and retract the sliding member 112. The casing of the handle 102 may have a cut out section 608 (or other suitable structure) on the side of the handle with the ports 114, 116 and port adapter 200 to allow for movement and sliding of the port adapter 200 and the sliding member 112 without interference from the casing of the handle 102.

FIG. 6B illustrates a close up, more detailed view of the roller assembly 600. The roller assembly 600 may comprise two side plates 602 on opposite sides of the roller assembly. The side plates 602 may be connected or attached to the handle 102 casing. The roller assembly 600 further comprises a plurality of rollers 604 extending between the two side plates 602. The roller assembly may have an number of rollers, for example, five rollers as shown in FIGS. 6A-B, but may alternatively have more or less. The rollers 604 may be any component capable of supporting and guiding the accessory channel 110 and enabling the accessory channels 110 to be advanced and retracted through the roller assembly 600 and/or tube 120. The rollers 604 may also prevent kinking or twisting of the accessory channel 110. The rollers 604 may spin with respect to the side plates 602. Alternatively, the rollers 604 may be stationary or fixed, with the accessory channel 110 sliding over the rollers 604. Each roller 604 may be a single, integral piece, or may comprise multiple components, such as a rod extending through the side plates 602 with rotating components that slide onto the rod and contact the accessory channels 110. The rollers 604 and end plates 603 may be made of, for example, plastic or metal material (or any other suitable material). The rollers may be coated with a friction reducing substance such as Teflon or silicone grease.

Figure 7:
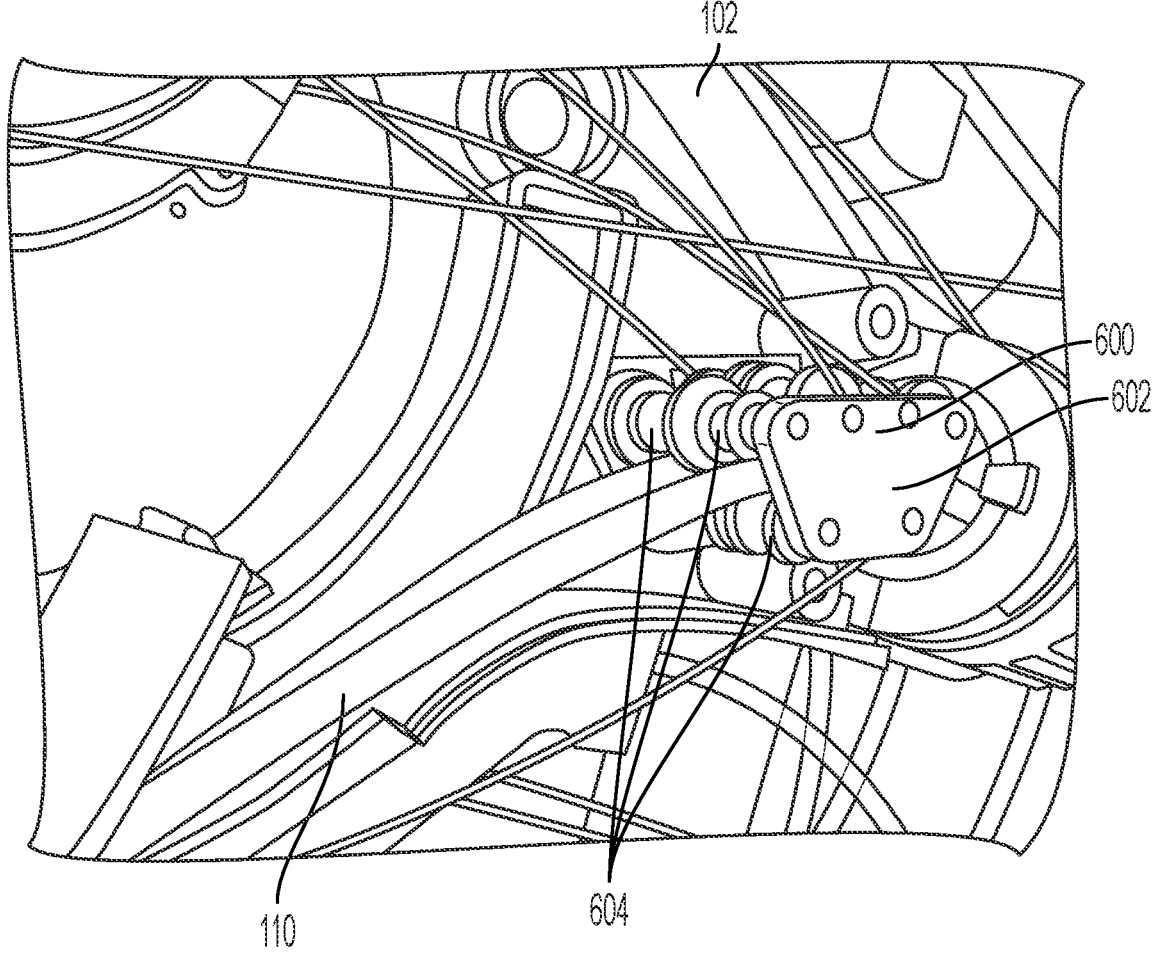
FIG. 7 illustrates another view of the roller assembly of the endoscopic system.

FIG. 7 illustrates another view of the endoscopic system 100 and roller assembly 600. FIG. 7 shows how one or more accessory channels 110 may extend through the roller assembly 600 before extending into the tube 120.

FIGS. 8A-D illustrate the distal end of the endoscopic system 100 shown in FIGS. 1-7. The distal portion or end 800 may have a flexible rib-like construction with multiple individual ribs 802 connected together to create an elongate tube of ribs. These ribs 802 may be made of a variety of materials, such as polycarbonate, nylon, polyethylene, polypropylene, and polyoxymethylene. The accessory channels 110 may travel through the ribs 802 to the distal portion 800. The distal end 800 may also include an opening 808 in the elongate tube of ribs that provides access to a point external the endoscope system 100. For example, when the endoscope system 100 is in the side-viewing position, a portion of the accessory channel 110 may protrude through the opening 808 of the elongete tube of ribs. The distal end 800 may include a pin 806, which may create a pivot point, around which the distal end may rotate to the position shown in FIG. 8C.

Figures 8A, 8B, 8C, 8D:
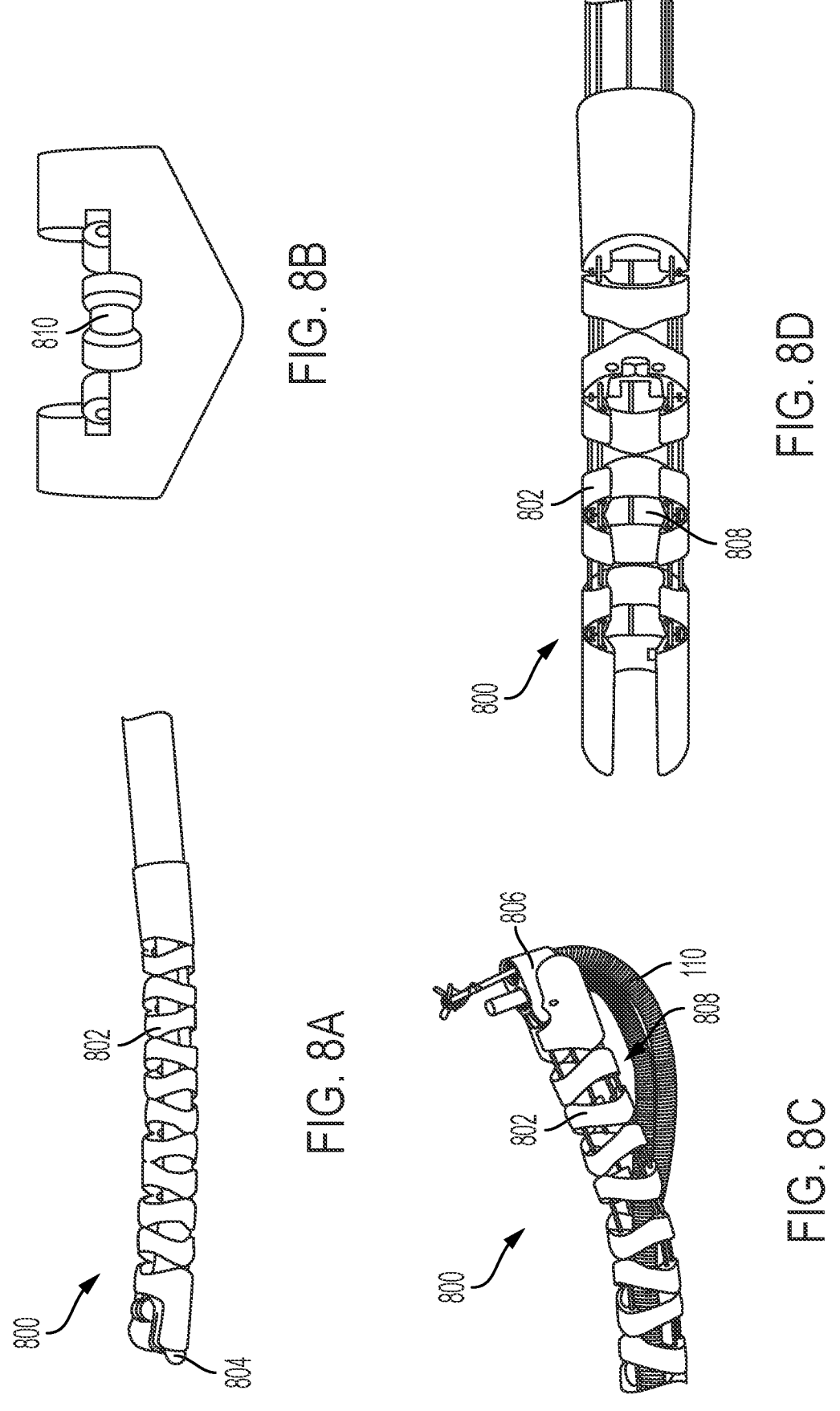
FIGS. 8A-D illustrate an example of a distal end of the endoscopic system.

The distal end 800 may be moved between a forward-viewing position as shown in FIG. 8A and a side-viewing position as shown in FIG. 8C. A LED light 804 may be placed on the distal end 800 to assist in navigation through a patient's body. The accessory channels 110 may rotate with the distal end 800 between the side-viewing and forward-viewing configurations. As can be seen in FIG. 8C, when in the side-viewing configuration, distal portions of the accessory channels 110 are bent outside of the confines of the ribs 802 and then curve back into the distal end 800. To facilitate movement between the two configurations, the ribs 802 may have a U or V-shaped design with an open section that allows the accessory channels 110 and/or tube 120 move freely in and out of the ribs 802.

To move the distal end 800 from the forward-viewing position to the side-viewing position, the accessory channels 110 and/or tube 120 may be pushed in a distal direction relative to the handle 102 and tube 120 which applies a force through the accessory channels 110 to the distal end 800. The resulting force causes the distal end 800 to rotate about the pivot point of the pin 806, thereby moving the accessory channels 110 and distal end 800 into the side-viewing configuration. To move back to the forward-viewing configuration, a proximal force may be applied to the accessory channels 110 relative to the handle 102 and tube 120, thereby transferring the proximal force to the distal end 800. The proximal force then causes the distal end 800 to again rotate around the pivot point of the pin 806 in the opposite direction, thereby moving the accessory channels 110 and the distal end 800 back to the forward-viewing configuration.

Due to this design, the ribs 802 may be shaped to allow for minimal contact between the individual ribs 802. For example, the ribs 802 shown in this embodiment have a substantially U-shaped cross-section with an opening and two sides. Each side of the ribs 802 may be diamond shaped when viewing the system 100 from a side angle. The diamond shape reduces the contact points between each rib 802, thus minimizing friction and allowing for easier bending of the distal portion 800 to the bent configuration and maximum flexibility.

The distal end 800 may include a roller 810 to facilitate movement of the tube 120 and/or accessory channels 110 through the distal end 800 and between the forward-viewing position and the side-viewing position. For example, the roller 810 may be disposed on the rib 802 immediately adjacent to the opening 808 of the elongate tube of ribs. Minimizing friction with the rollers increases force transmission tubing to prevent formation of kinks in the tubing or accessories. The ribs 802 may contain one or more rollers 810 proximal to the distal end 800. For example, the may be multiple rollers 810, each on a respective rib 802, such that the rollers 810 are spaced at different points along the distal end 800. Additionally or alternatively, a sinlge rib 802 may include one or more rollers 810 on the rib 802. The roller 810 may be any type of suitable roller for assisting the extension and retraction of tubing and/or accessories, for example, of the tube 120, the accessory channels 110, and/or of accessories passed through the accessory channels 110. The roller 810 may be, for example, a cylindrical roller 810 disposed over a pin fixed in the the rib 802 such that the cylindrical roller 810 is fee to rotate. Additional or alternatively, the roller 810 may be, for example, a bearing. The roller 810 may be, for example, plastic, metal, composite, or any other suitable matieral. The roller 810 may be made of the same material as the ribs 802. Additionally or alternative, the roller 810 may be a different material from the ribs 802.

The endoscope system 100 described herein may be used for a variety of medical procedures. While the embodiments described herein are shown in reference to the endoscopy field and endoscopic retrograde cholangiopancreatography procedures, the embodiments may be used in a variety of other medical procedures including endoscopic submucosal dissection and any other endoscopic procedure that would benefit by having multiple instruments at a time and/or the ability to see things from both the forward-viewing and side-viewing perspectives.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An endoscopic device, the endoscopic device comprising:
   a distal end;
   a proximal end;

a handle at the proximal end;

a tube extending from the handle towards the distal end of the endoscopic device;

an accessory channel extending at least partially through the tube;

a slide, the accessory channel coupled to the slide; and a curved track included in the handle, wherein at least a portion of the curved track is disposed proximal to the tube, wherein the slide is movable within the curved track to cause movement of the accessory channel within the tube.

2. The device of claim 1, wherein the accessory channel extends through the slide.

3. The device of claim 1 further comprising an access port connected to the slide that provides access to the accessory channel.

4. The device of claim 3 wherein the slide is fixed relative to the access port such that the access port moves when the slide moves within the curved track.

5. The device of claim 3 further comprising a port adapter connected to the access port and accessory channel.

6. The device of claim 1 further comprising a roller assembly disposed in the handle, the roller assembly including one or more rollers, wherein the roller assembly supports the accessory channel when the accessory channel is advanced towards the distal end.

7. The device of claim 6, wherein the one or more rollers are arranged in rows such that the accessory channel fits between the rows of the rollers.

8. The device of claim 6, wherein the roller assembly is disposed at a distal most end of the handle proximal to the tube.

9. The device of claim 1 wherein the slide can be locked in place while the accessory channel is advanced.

10. The device of claim 1 further comprising a lock, wherein the lock is configured to prevent movement of the slide relative to the curved track.

11. The device of claim 1 wherein the handle comprises a circular section, wherein the curved track follows a curve of the circular section.

12. The device of claim 1 further comprising a camera disposed near the distal end of the endoscopic device.

13. The device of claim 1 further comprising a ribbed structure at the distal end of the device, wherein at least one rib of the ribbed structure includes a roller.

14. The device of claim 1, wherein the handle comprises a curved portion, wherein a radius of the curved track matches a radius of the curved portion of the handle.

15. The device of claim 1, wherein the curved track is defined at least partially by a non-linear shape of the handle.

16. The device of claim 1, wherein the slide has a curved contour that matches a curved contour of the curved track.

17. An A scope system, the scope system comprising:

a distal end;

a proximal end opposite the distal end;

a handle at the proximal end;

a tube extending from the handle towards the distal end of the endoscopic device;

an accessory channel extending through the tube;

a slide, the accessory channel coupled to the slide;

a track included in the handle and disposed proximal to the tube;

an access port integrated with the slide, such that the access port moves when the slide moves within the track; and a camera disposed near the distal end of the scope system, wherein the slide is movable within the track to cause movement of the accessory channel and the access port with respect to the tube.

18. The system of claim 17 wherein the slide is fixed relative to the access port such that the access port moves when the slide moves within the track.

19. The system of claim 17, wherein the scope system comprises a ribbed structure at the distal end of the system, the ribbed structure comprising one or more ribs, wherein at least one rib includes a roller.

20. The system of claim 17 further comprising a roller disposed near the distal end of the scope system.

* * * * *